United States Patent
Revuelta Doval et al.

(10) Patent No.: US 6,929,933 B1
(45) Date of Patent: Aug. 16, 2005

(54) RIBOFLAVIN SYNTHESIS IN YEAST

(75) Inventors: José Luis Revuelta Doval, Salamanca (ES); Maria Angeles Santos Garcia, Santa Marta (ES); José Javier Garcia-Ramirez, Nalda (ES); Gloria Angélica González-Hernández, Aquascalientes (MX); Maria José Buitrago Serna, Salamanca (ES)

(73) Assignee: BASF AG, Ludwigshafen (DE)

( * ) Notice: Subject to any disclaimer, the term of this patent is extended or adjusted under 35 U.S.C. 154(b) by 585 days.

(21) Appl. No.: 08/989,140

(22) Filed: Dec. 11, 1997

Related U.S. Application Data

(63) Continuation of application No. 08/403,768, filed as application No. PCT/EP93/03183 on Nov. 12, 1993, now abandoned.

(30) Foreign Application Priority Data

Nov. 19, 1992 (DE) ....................... P 42 38 904

(51) Int. Cl.[7] .............................................. C12P 17/18
(52) U.S. Cl. ....................................................... 435/119
(58) Field of Search .......................................... 435/119

(56) References Cited

FOREIGN PATENT DOCUMENTS

EP           0 405 370 A1 * 1/1991

OTHER PUBLICATIONS

Revuelta et al. (1990) Biosynthesis of Vitamin B2 in Yeast. In Organizing Committee of Biotec–90 (Eds). From Genes to Bioproducts, DM PPU, Murcia, Spain, pp. 117–122.*
Oltmanns et al. Biochemical and Genetic Classification of Riboflavine Deficient Mutants of Saccharomyces cerevisiae. Molec. Gen. Genetics (1969) 105: 306–313.*

* cited by examiner

*Primary Examiner*—Kathleen Kerr
(74) *Attorney, Agent, or Firm*—Novak Druce & Quigg, LLP

(57) ABSTRACT

The invention describes the riboflavin biosynthesis gene and gene products from yeast. Vectors and recombinant preparation processes for riboflavin are furthermore described. Specifically, the invention relates to the genes for riboflavin biosynthesis in yeast, the proteins encoded therewith and genetic engineering process for the preparation of riboflavin using these genes and gene products. Accordingly, six genes (rib genes), which encode from enzymes of riboflavin biosynthesis starting from GTP, were found in the yeast *Saccharomyces cerevisiae* and isolated.

1 Claim, 6 Drawing Sheets

SEQUENCE LISTING

```
<160> NUMBER OF SEQ ID NOS: 12

<210> SEQ ID NO 1
<211> LENGTH: 1748
<212> TYPE: DNA
<213> ORGANISM: Saccharomyces cerevisiae
<220> FEATURE:
<221> NAME/KEY: 5'UTR
<222> LOCATION: (1)..(258)
<221> NAME/KEY: CDS
<222> LOCATION: (259)..(1296)
<221> NAME/KEY: 3'UTR
<222> LOCATION: (1297)..(1748)

<400> SEQUENCE: 1
tctagactta gcatagggct aaaacagaaa tagtagggtc tataccgttt ttgaaaacaa         60
gttgtgtagg gtgagacttt ttcttttcc tttgagtttt tcttttctt tttacgattt        120 gtcagaaatt agtcggacgc tcttgtgggg tgagcgccag gccgctatag tatatataaa        180
gaagttgctg tgctggcgtg gacaataatt gagtcattac aaaaagtggc gtacataaaa        240
ctacaacaaa cctacagg atg acc ata gat aac tac gac aac agt aaa cag         291
                     Met Thr Ile Asp Asn Tyr Asp Asn Ser Lys Gln
                      1               5                  10 gat agc agc aaa tac gag gtt agt ggt acg ggt gat ggc agg aac ggc         339
Asp Ser Ser Lys Tyr Glu Val Ser Gly Thr Gly Asp Gly Arg Asn Gly
         15                  20                  25 gat ggc ggc ttg cct cta gta caa tgt gtc gca aga gct cgt atc cca         387
Asp Gly Gly Leu Pro Leu Val Gln Cys Val Ala Arg Ala Arg Ile Pro
     30                  35                  40 acc aca cag ggt ccg gat atc ttt tta cat ctt tac agt aac aac agg         435
Thr Thr Gln Gly Pro Asp Ile Phe Leu His Leu Tyr Ser Asn Asn Arg
 45                  50                  55 gac aac aag gaa cat cta gcc att gtg ttt ggt gaa gac ata cgg tcg         483
Asp Asn Lys Glu His Leu Ala Ile Val Phe Gly Glu Asp Ile Arg Ser
 60                  65                  70                  75 cgc tcg cta ttc cgt aga aga cag tgc gag acg caa caa gat aga atg         531
Arg Ser Leu Phe Arg Arg Arg Gln Cys Glu Thr Gln Gln Asp Arg Met
             80                  85                  90 atc agg ggc gct tat att ggc aaa ctg tat ccc ggc aga act gtg gca         579
```

|   |   |
|---|---|
| Ile Arg Gly Ala Tyr Ile Gly Lys Leu Tyr Pro Gly Arg Thr Val Ala<br>                95                        100                        105 |   |
| gac gaa gac gat aga ctc gga tta gct ctg gag ttt gat gat agt aca<br>Asp Glu Asp Asp Arg Leu Gly Leu Ala Leu Glu Phe Asp Asp Ser Thr<br>            110                        115                      120 | 627 |
| ggt gag tta tta gct tcc aaa gcc act aca tgg gac gcc cat aac gac<br>Gly Glu Leu Leu Ala Ser Lys Ala Thr Thr Trp Asp Ala His Asn Asp<br>      125                        130                      135 | 675 |
| acg ctg gta cgg atc cat tct gaa tgt tac acc ggt gaa aac gca tgg<br>Thr Leu Val Arg Ile His Ser Glu Cys Tyr Thr Gly Glu Asn Ala Trp<br>140                      145                      150                      155 | 723 |
| agc gcc cgt tgt gat tgt ggt gaa caa ttc gat agg gcc ggt agg ctt<br>Ser Ala Arg Cys Asp Cys Gly Glu Gln Phe Asp Arg Ala Gly Arg Leu<br>                    160                        165                      170 | 771 |
| atc gct tgc gac cac gaa ccc aca agc aac atc aaa ggt gga aac ggc<br>Ile Ala Cys Asp His Glu Pro Thr Ser Asn Ile Lys Gly Gly Asn Gly<br>                175                        180                        185 | 819 |
| cat ggt gtt atc gtg tat cta aga caa gag ggt cgt ggc atc ggg tta<br>His Gly Val Ile Val Tyr Leu Arg Gln Glu Gly Arg Gly Ile Gly Leu<br>          190                        195                      200 | 867 |
| ggt gag aaa ctc aag gcc tac aac ctg caa gac tta ggt gct gac aca<br>Gly Glu Lys Leu Lys Ala Tyr Asn Leu Gln Asp Leu Gly Ala Asp Thr<br>205                      210                      215 | 915 |
| gtg cag gcc aac tta atg ctg aaa cat ccc gtg gat gct agg gac ttc<br>Val Gln Ala Asn Leu Met Leu Lys His Pro Val Asp Ala Arg Asp Phe<br>220                      225                      230                      235 | 963 |
| tcg ctg ggt aag gct att ttg ctg gat ctt ggc atc ggt aat gtc agg<br>Ser Leu Gly Lys Ala Ile Leu Leu Asp Leu Gly Ile Gly Asn Val Arg<br>                    240                        245                      250 | 1011 |
| ctg ctg aca aat aac ccg gaa aag ata aaa cag gta gat cat gcg cct<br>Leu Leu Thr Asn Asn Pro Glu Lys Ile Lys Gln Val Asp His Ala Pro<br>                255                        260                        265 | 1059 |
| tac ctt aag tgc gtt gaa cga gtg cct atg gta ccc ata cac tgg aca<br>Tyr Leu Lys Cys Val Glu Arg Val Pro Met Val Pro Ile His Trp Thr<br>          270                        275                      280 | 1107 |
| aac tcc agt gaa ggc ata gac tcc aag gag ata gaa ggt tat ctc agg<br>Asn Ser Ser Glu Gly Ile Asp Ser Lys Glu Ile Glu Gly Tyr Leu Arg<br>285                      290                      295 | 1155 |
| acc aag ata gaa aga atg ggt cat tta cta acg gag cct ctg aaa ctt<br>Thr Lys Ile Glu Arg Met Gly His Leu Leu Thr Glu Pro Leu Lys Leu<br>300                      305                      310                      315 | 1203 |
| cat aca aac cct caa cct act gag aca agt gaa gcc caa aac caa aac<br>His Thr Asn Pro Gln Pro Thr Glu Thr Ser Glu Ala Gln Asn Gln Asn<br>                320                        325                      330 | 1251 |
| cgt atg aac tct gcg ttg tca tca aca tcg acg ctg gca ata taa<br>Arg Met Asn Ser Ala Leu Ser Ser Thr Ser Thr Leu Ala Ile<br>              335                        340                      345 | 1296 |
| acacaagtgt agcataatta ttagtacata tagtgctttt tttgtaatga acgaaaata | 1356 |
| ccatgttatt ttaatgcgtt accccgtcgg cgcgtattgg cgcattaaca tctttataga | 1416 |
| aaatcaaatt atttacttat ttattctaaa acgctaaaca tctatttatt tacatttgag | 1476 |
| gttgaaactt cccttcatcc gattgacagg catatttagc ggtaattatt agggtttttg | 1536 |
| gagagacctt gtattcttca gaaataatgt cgtccttcaa caatgagacc aataataaca | 1596 |
| gcaaacacta atacacatcc agacgattcc ttccctttgt ataccgtatt caaggacgag | 1656 |
| tctgtaccca tcgaggaaaa aatggcactg cttacacggt tcaaaggaca tgtaaaaaag | 1716 |
| gaactagtta acgaatcgtc gatccaagct td | 1748 |

<210> SEQ ID NO 2
<211> LENGTH: 345
<212> TYPE: PRT
<213> ORGANISM: Saccharomyces cerevisiae

<400> SEQUENCE: 2

```
Met Thr Ile Asp Asn Tyr Asp Asn Ser Lys Gln Asp Ser Ser Lys Tyr
  1               5                  10                  15

Glu Val Ser Gly Thr Gly Asp Gly Arg Asn Gly Asp Gly Leu Pro
             20                  25                  30

Leu Val Gln Cys Val Ala Arg Ala Arg Ile Pro Thr Thr Gln Gly Pro
             35                  40                  45

Asp Ile Phe Leu His Leu Tyr Ser Asn Asn Arg Asp Asn Lys Glu His
         50                  55                  60

Leu Ala Ile Val Phe Gly Glu Asp Ile Arg Ser Arg Ser Leu Phe Arg
 65                  70                  75                  80

Arg Arg Gln Cys Glu Thr Gln Gln Asp Arg Met Ile Arg Gly Ala Tyr
                 85                  90                  95

Ile Gly Lys Leu Tyr Pro Gly Arg Thr Val Ala Asp Glu Asp Asp Arg
            100                 105                 110

Leu Gly Leu Ala Leu Glu Phe Asp Asp Ser Thr Gly Glu Leu Leu Ala
            115                 120                 125

Ser Lys Ala Thr Thr Trp Asp Ala His Asn Asp Thr Leu Val Arg Ile
        130                 135                 140

His Ser Glu Cys Tyr Thr Gly Glu Asn Ala Trp Ser Ala Arg Cys Asp
145                 150                 155                 160

Cys Gly Glu Gln Phe Asp Arg Ala Gly Arg Leu Ile Ala Cys Asp His
                165                 170                 175

Glu Pro Thr Ser Asn Ile Lys Gly Gly Asn Gly His Gly Val Ile Val
            180                 185                 190

Tyr Leu Arg Gln Glu Gly Arg Gly Ile Gly Leu Gly Glu Lys Leu Lys
            195                 200                 205

Ala Tyr Asn Leu Gln Asp Leu Gly Ala Asp Thr Val Gln Ala Asn Leu
        210                 215                 220

Met Leu Lys His Pro Val Asp Ala Arg Asp Phe Ser Leu Gly Lys Ala
225                 230                 235                 240

Ile Leu Leu Asp Leu Gly Ile Gly Asn Val Arg Leu Leu Thr Asn Asn
                245                 250                 255

Pro Glu Lys Ile Lys Gln Val Asp His Ala Pro Tyr Leu Lys Cys Val
            260                 265                 270

Glu Arg Val Pro Met Val Pro Ile His Trp Thr Asn Ser Ser Glu Gly
            275                 280                 285

Ile Asp Ser Lys Glu Ile Glu Gly Tyr Leu Arg Thr Lys Ile Glu Arg
        290                 295                 300

Met Gly His Leu Leu Thr Glu Pro Leu Lys Leu His Thr Asn Pro Gln
305                 310                 315                 320

Pro Thr Glu Thr Ser Glu Ala Gln Asn Gln Asn Arg Met Asn Ser Ala
                325                 330                 335

Leu Ser Ser Thr Ser Thr Leu Ala Ile
            340                 345
```

<210> SEQ ID NO 3
<211> LENGTH: 3087
<212> TYPE: DNA
<213> ORGANISM: Saccharomyces cerevisiae -continued

```
<220> FEATURE:
<221> NAME/KEY: 5'UTR
<222> LOCATION: (1)..(592)
<221> NAME/KEY: CDS
<222> LOCATION: (593)..(2368)
<221> NAME/KEY: 3'UTR
<222> LOCATION: (2369)..(3087)

<400> SEQUENCE: 3
```

| | | | | |
|---|---|---|---|---|
| atgagcccga | agtgggagcg | cgcgatcttg | ccccatcggt | gatgtcggcg atataggcgc | 60 |
| cagacaccgc | acctgtggcg | ccggtgatgc | cgcacgatgc | gtccggcgta gaggatcatc | 120 |
| aacccgttaa | tcttaccgta | agattaccaa | ggtctacagg | gacgccagtg ccttatcctt | 180 |
| acatatcgaa | agtatccttt | atcatggagc | tctggcctga | ttggacaaat tggtgacgca | 240 |
| gtcatcgggt | actgcggttg | gctagttact | aagaatgtac | attattggat attaggttct | 300 |
| ttactattat | atttactatt | aaaaatcctg | taaagtgatc | tgggctgtca ggctagaagt | 360 |
| ttttcattta | tgtctgaaac | agataacgtc | agttgtacca | ctatctttgg ttttattctt | 420 |
| tttattttct | cttccatata | tctttacaga | acttaagtaa | taatgaaaaa gaatgaaaaa | 480 |
| aaaaaaaaaa | aaagaaaaac | tagtcaaaat | tattgccatg | aaaaaacagg aagaagagag | 540 |
| aagaacatta | aaaaaaaaaa | actatcaata | ttagattaac | aaaccaatca aa atg gag | 598 |
| | | | | Met Glu |
| | | | | 1 |

| | | | | |
|---|---|---|---|---|
| gac tct aat aat gaa gcc agc gat gac ttc aac aac tta tta aac aaa | 646 |
| Asp Ser Asn Asn Glu Ala Ser Asp Asp Phe Asn Asn Leu Leu Asn Lys | |
| 5 10 15 | |

| | |
|---|---|
| gaa att gag tct gca aag gaa gtg aag tta aga aaa ttc gcg aac agg | 694 |
| Glu Ile Glu Ser Ala Lys Glu Val Lys Leu Arg Lys Phe Ala Asn Arg | |
| 20 25 30 | |

| | |
|---|---|
| aat aat aat agg aac gaa aac agt tcc aaa gtc aaa gat gcg agt gga | 742 |
| Asn Asn Asn Arg Asn Glu Asn Ser Ser Lys Val Lys Asp Ala Ser Gly | |
| 35 40 45 50 | |

| | |
|---|---|
| ttc aga ctg aga gtt att caa acc gat ggg cac aaa act aaa aag aca | 790 |
| Phe Arg Leu Arg Val Ile Gln Thr Asp Gly His Lys Thr Lys Lys Thr | |
| 55 60 65 | |

| | |
|---|---|
| gac cct gat tat gaa gtg aca att gat gga ccc tta agg aag att gag | 838 |
| Asp Pro Asp Tyr Glu Val Thr Ile Asp Gly Pro Leu Arg Lys Ile Glu | |
| 70 75 80 | |

| | |
|---|---|
| cct tat ttt ttc act tat aaa act ttc tgt aag gag agg tgg aga gat | 886 |
| Pro Tyr Phe Phe Thr Tyr Lys Thr Phe Cys Lys Glu Arg Trp Arg Asp | |
| 85 90 95 | |

| | |
|---|---|
| cgt aag ttg gtg gat gta ttc gtg agc gaa ttc agg gat cga gag ccc | 934 |
| Arg Lys Leu Val Asp Val Phe Val Ser Glu Phe Arg Asp Arg Glu Pro | |
| 100 105 110 | |

| | |
|---|---|
| agc tat tat tcc aaa acc att gca gag gga aaa gta tac tta aac gat | 982 |
| Ser Tyr Tyr Ser Lys Thr Ile Ala Glu Gly Lys Val Tyr Leu Asn Asp | |
| 115 120 125 130 | |

| | |
|---|---|
| gaa cct gca aac ctt gat acc atc att cgt gac ggt gat ctg atc aca | 1030 |
| Glu Pro Ala Asn Leu Asp Thr Ile Ile Arg Asp Gly Asp Leu Ile Thr | |
| 135 140 145 | |

| | |
|---|---|
| cat aaa gta cat cga cat gaa ccg cca gtc aca tct aaa cca ata gat | 1078 |
| His Lys Val His Arg His Glu Pro Pro Val Thr Ser Lys Pro Ile Asp | |
| 150 155 160 | |

| | |
|---|---|
| att gtg ttt gaa gac gaa gat atc ctt gtc att gat aaa ccc agc agt | 1126 |
| Ile Val Phe Glu Asp Glu Asp Ile Leu Val Ile Asp Lys Pro Ser Ser | |
| 165 170 175 | |

| | |
|---|---|
| att cca gtg cac cca acg ggc aga tac aga ttc aat acc att aca aaa | 1174 |
| Ile Pro Val His Pro Thr Gly Arg Tyr Arg Phe Asn Thr Ile Thr Lys | |
| 180 185 190 | |

```
atg cta gaa aga cag cta ggt tat tca gta cat cca tgt aat aga cta      1222
Met Leu Glu Arg Gln Leu Gly Tyr Ser Val His Pro Cys Asn Arg Leu
195                 200                 205                 210 gac aag cca act agt gga cta atg ttt tta gcc aag act cca tta ggt      1270
Asp Lys Pro Thr Ser Gly Leu Met Phe Leu Ala Lys Thr Pro Leu Gly
                215                 220                 225 gca gat aga atg gga gac caa atg aaa gcg agg gaa gtc acc aaa gaa      1318
Ala Asp Arg Met Gly Asp Gln Met Lys Ala Arg Glu Val Thr Lys Glu
            230                 235                 240 tac gta gcc cgc gtg aag ggc gag ttc cct ata ggt ata gta gag gta      1366
Tyr Val Ala Arg Val Lys Gly Glu Phe Pro Ile Gly Ile Val Glu Val
        245                 250                 255 gat aag cct gtc aga tct gtt aac cct aaa gtt gca cta aac gct gtt      1414
Asp Lys Pro Val Arg Ser Val Asn Pro Lys Val Ala Leu Asn Ala Val
    260                 265                 270 tgc gag atg agc gat gaa aac gct aaa cat gcc aag acc gtt ttc caa      1462
Cys Glu Met Ser Asp Glu Asn Ala Lys His Ala Lys Thr Val Phe Gln
275                 280                 285                 290 agg gtt agc tat gat gga cag acg agt att gta aag tgt aaa cca ttg      1510
Arg Val Ser Tyr Asp Gly Gln Thr Ser Ile Val Lys Cys Lys Pro Leu
                295                 300                 305 aca ggt aga act cac caa ata aga gtc cat ttg cag tac ttg gga ttt      1558
Thr Gly Arg Thr His Gln Ile Arg Val His Leu Gln Tyr Leu Gly Phe
            310                 315                 320 ccc ata gca aat gac cct ata tac tcg aac cca gat atc tgg ggt cca      1606
Pro Ile Ala Asn Asp Pro Ile Tyr Ser Asn Pro Asp Ile Trp Gly Pro
        325                 330                 335 gat ttg ggc cgc ggt gga ctt caa aac tat gat gac atc gtt ctg aaa      1654
Asp Leu Gly Arg Gly Gly Leu Gln Asn Tyr Asp Asp Ile Val Leu Lys
    340                 345                 350 cta gac gct att ggc aag act aat cct gca gag agc tgg att cat cct      1702
Leu Asp Ala Ile Gly Lys Thr Asn Pro Ala Glu Ser Trp Ile His Pro
355                 360                 365                 370 cat agc gag ggt gaa tac ttg ctt ggc cgt cag tgc gaa gaa tgc gag      1750
His Ser Glu Gly Glu Tyr Leu Leu Gly Arg Gln Cys Glu Glu Cys Glu
                375                 380                 385 gct gaa atg tac aca gat ccc ggt act aat gat ctc gac ctc tgg ctg      1798
Ala Glu Met Tyr Thr Asp Pro Gly Thr Asn Asp Leu Asp Leu Trp Leu
            390                 395                 400 cat gcc ttc cgg tac gag tca ttg gaa aga aat tcg gat acg caa aaa      1846
His Ala Phe Arg Tyr Glu Ser Leu Glu Arg Asn Ser Asp Thr Gln Lys
        405                 410                 415 cct ctc tgg agt tat aga aca aaa tac cct gaa tgg gcc tta gag cca      1894
Pro Leu Trp Ser Tyr Arg Thr Lys Tyr Pro Glu Trp Ala Leu Glu Pro
    420                 425                 430 cat cgc cga tat atg gaa atg gcc gtt aag gaa gct ggt aag tgt ggc      1942
His Arg Arg Tyr Met Glu Met Ala Val Lys Glu Ala Gly Lys Cys Gly
435                 440                 445                 450 ccg aca aag act gct ttt agt gtt ggt gcc gtt ctt gtt cat gga act      1990
Pro Thr Lys Thr Ala Phe Ser Val Gly Ala Val Leu Val His Gly Thr
                455                 460                 465 caa gta ctt gcc aca gga tat tca aga gag cta cca gga aac act cat      2038
Gln Val Leu Ala Thr Gly Tyr Ser Arg Glu Leu Pro Gly Asn Thr His
            470                 475                 480 gca gaa cag tgt gct ttg ata aag tac tcg cag tta cac ccg aac tgt      2086
Ala Glu Gln Cys Ala Leu Ile Lys Tyr Ser Gln Leu His Pro Asn Cys
        485                 490                 495 ccc act ata gtc cct atg gga aca gtg ctc tat aca acc atg gaa ccc      2134
Pro Thr Ile Val Pro Met Gly Thr Val Leu Tyr Thr Thr Met Glu Pro
```

-continued

```
                  500                 505                 510
tgt tcc ttc agg cta agt ggc aat gag cct tgc tgc gat aga atc ctg      2182
Cys Ser Phe Arg Leu Ser Gly Asn Glu Pro Cys Cys Asp Arg Ile Leu
515                 520                 525                 530 gcc acc caa ggt gcc att ggt act gtc ttc gtg ggg gtt atg gag ccc      2230
Ala Thr Gln Gly Ala Ile Gly Thr Val Phe Val Gly Val Met Glu Pro
                535                 540                 545 gat aca ttt gtt aaa aac aat aca agt ttg aac aag ctg gaa tcg cac      2278
Asp Thr Phe Val Lys Asn Asn Thr Ser Leu Asn Lys Leu Glu Ser His
            550                 555                 560 ggt gtg aac tac ata caa ata cca ggc tac gag gag gag tgc acc atc      2326
Gly Val Asn Tyr Ile Gln Ile Pro Gly Tyr Glu Glu Glu Cys Thr Ile
        565                 570                 575 att gcc ttc aaa ggc cac gat aat agt gac gac aaa gct tag              2368
Ile Ala Phe Lys Gly His Asp Asn Ser Asp Asp Lys Ala
    580                 585                 590 actatttagc atatatatta tcatgtaatc ttcatcata tctacaataa ccactcatta    2428
ctggaaacgg aaaaaggcgc accgaaaat tttgagtaaa agaatggaa ttaacttcaa     2488 ccacaacaca gacaaaaaac actagatagt gaaccaaaag aaagcacaac accaaacatg   2548
agcagcattc cagctggcac tgatcctggg tcctgcggtg ctaatttcaa gaatgaccgc   2608
aagcgcagag ataagatcaa cgaccgtatt caagaactat tgagtatcat tcccaaagac  2668
ttctttagag attattacgg caattctggt agcaatgaca cgttaagtga atccactccc  2728
ggtgcgcttg ggttgtccag caaggccaaa ggtacaggga ccaaggacgg aaagcccaac   2788
aagggccaaa ttctcacaca ggcggtagag tacatatcac atctacaaaa tcaagtggac   2848
acacagaaca gagaggaggt ggaactgatg gtgaaggcca ctcagttggc caagcagaca   2908
ggcaccattg tcaacgatat aaacttagag aacaccagcg ctgaagtcgc cctgtccagg   2968
attggcgtgg gaccgctggc cgcaacaaat gatgactcag taagaccgcc agcaaagagg   3028
ttgagctcct tcgagtacgg agggtatggt gagtacggta atggtagcta aaagtactd    3087
```

<210> SEQ ID NO 4
<211> LENGTH: 591
<212> TYPE: PRT
<213> ORGANISM: Saccharomyces cerevisiae

<400> SEQUENCE: 4

```
Met Glu Asp Ser Asn Asn Glu Ala Ser Asp Asp Phe Asn Asn Leu Leu
1               5                   10                  15

Asn Lys Glu Ile Glu Ser Ala Lys Glu Val Lys Leu Arg Lys Phe Ala
            20                  25                  30

Asn Arg Asn Asn Asn Arg Asn Glu Asn Ser Ser Lys Val Lys Asp Ala
        35                  40                  45

Ser Gly Phe Arg Leu Arg Val Ile Gln Thr Asp Gly His Lys Thr Lys
    50                  55                  60

Lys Thr Asp Pro Asp Tyr Glu Val Thr Ile Asp Gly Pro Leu Arg Lys
65                  70                  75                  80

Ile Glu Pro Tyr Phe Phe Thr Tyr Lys Thr Phe Cys Lys Glu Arg Trp
                85                  90                  95

Arg Asp Arg Lys Leu Val Asp Val Phe Val Ser Glu Phe Arg Asp Arg
            100                 105                 110

Glu Pro Ser Tyr Tyr Ser Lys Thr Ile Ala Glu Gly Lys Val Tyr Leu
        115                 120                 125

Asn Asp Glu Pro Ala Asn Leu Asp Thr Ile Ile Arg Asp Gly Asp Leu
```

-continued

```
            130                 135                 140
Ile Thr His Lys Val His Arg His Glu Pro Pro Val Thr Ser Lys Pro
145                 150                 155                 160

Ile Asp Ile Val Phe Glu Asp Asp Ile Leu Val Ile Asp Lys Pro
                165                 170                 175

Ser Ser Ile Pro Val His Pro Thr Gly Arg Tyr Arg Phe Asn Thr Ile
                180                 185                 190

Thr Lys Met Leu Glu Arg Gln Leu Gly Tyr Ser Val His Pro Cys Asn
                195                 200                 205

Arg Leu Asp Lys Pro Thr Ser Gly Leu Met Phe Leu Ala Lys Thr Pro
210                 215                 220

Leu Gly Ala Asp Arg Met Gly Asp Gln Met Lys Ala Arg Glu Val Thr
225                 230                 235                 240

Lys Glu Tyr Val Ala Arg Val Lys Gly Glu Phe Pro Ile Gly Ile Val
                245                 250                 255

Glu Val Asp Lys Pro Val Arg Ser Val Asn Pro Lys Val Ala Leu Asn
                260                 265                 270

Ala Val Cys Glu Met Ser Asp Glu Asn Ala Lys His Ala Lys Thr Val
                275                 280                 285

Phe Gln Arg Val Ser Tyr Asp Gly Gln Thr Ser Ile Val Lys Cys Lys
                290                 295                 300

Pro Leu Thr Gly Arg Thr His Gln Ile Arg Val His Leu Gln Tyr Leu
305                 310                 315                 320

Gly Phe Pro Ile Ala Asn Asp Pro Ile Tyr Ser Asn Pro Asp Ile Trp
                325                 330                 335

Gly Pro Asp Leu Gly Arg Gly Gly Leu Gln Asn Tyr Asp Asp Ile Val
                340                 345                 350

Leu Lys Leu Asp Ala Ile Gly Lys Thr Asn Pro Ala Glu Ser Trp Ile
                355                 360                 365

His Pro His Ser Glu Gly Glu Tyr Leu Leu Gly Arg Gln Cys Glu Glu
                370                 375                 380

Cys Glu Ala Glu Met Tyr Thr Asp Pro Gly Thr Asn Asp Leu Asp Leu
385                 390                 395                 400

Trp Leu His Ala Phe Arg Tyr Glu Ser Leu Glu Arg Asn Ser Asp Thr
                405                 410                 415

Gln Lys Pro Leu Trp Ser Tyr Arg Thr Lys Tyr Pro Glu Trp Ala Leu
                420                 425                 430

Glu Pro His Arg Arg Tyr Met Glu Met Ala Val Lys Glu Ala Gly Lys
                435                 440                 445

Cys Gly Pro Thr Lys Thr Ala Phe Ser Val Gly Ala Val Leu Val His
450                 455                 460

Gly Thr Gln Val Leu Ala Thr Gly Tyr Ser Arg Glu Leu Pro Gly Asn
465                 470                 475                 480

Thr His Ala Glu Gln Cys Ala Leu Ile Lys Tyr Ser Gln Leu His Pro
                485                 490                 495

Asn Cys Pro Thr Ile Val Pro Met Gly Thr Val Leu Tyr Thr Thr Met
                500                 505                 510

Glu Pro Cys Ser Phe Arg Leu Ser Gly Asn Glu Pro Cys Cys Asp Arg
                515                 520                 525

Ile Leu Ala Thr Gln Gly Ala Ile Gly Thr Val Phe Val Gly Val Met
                530                 535                 540

Glu Pro Asp Thr Phe Val Lys Asn Asn Thr Ser Leu Asn Lys Leu Glu
545                 550                 555                 560
```

-continued

Ser His Gly Val Asn Tyr Ile Gln Ile Pro Gly Tyr Glu Glu Cys
              565                 570                 575

Thr Ile Ile Ala Phe Lys Gly His Asp Asn Ser Asp Asp Lys Ala
              580                 585                 590

<210> SEQ ID NO 5
<211> LENGTH: 1530
<212> TYPE: DNA
<213> ORGANISM: Saccharomyces cerevisiae
<220> FEATURE:
<221> NAME/KEY: 5'UTR
<222> LOCATION: (1)..(522)
<221> NAME/KEY: CDS
<222> LOCATION: (523)..(1149)
<221> NAME/KEY: 3'UTR
<222> LOCATION: (1150)..(1530)

<400> SEQUENCE: 5

```
ctgcagaaaa ccactctacg agggtaacct gtagagttta cttgggacga tgctcggcgg      60
ctaatgcttc tattatcatg ttccacggac tggacggtgc ggctctggga cgcgcgagca     120
gggaaaggta tcatagggc gccattatta ttaggggggc ccgtactacg tgcacgctgg      180
ctcgaaaaaa acaatggagg ggaaaatagt cgcactctac ggtgtcaagt gtggtgtgca     240
gatggtcgcc tcgttgttgt aaattgggct ttcgatgcta agacgtccct ctacacggcc     300
actgttatct cctaacgccg cttcgaggcg ggtgagcata ggttattgcc tgatgagtaa     360
tttcttagcg agaattgata aaaaaaagca aggctattat taatatacgt gctattgtga     420
aattttcatt ggcgtatata tgtgaggtga atgtaaatat ctccaacaaa aagcagaagg     480
ctaaaaaaaa ggaaaggaaa agaagaaaag gcaacgtcga aa atg ttt aca cca        534
                                                Met Phe Thr Pro
                                                  1 att gat caa gct ata gaa cac ttc aag cag aat aag ttt gta att gtt       582
Ile Asp Gln Ala Ile Glu His Phe Lys Gln Asn Lys Phe Val Ile Val
  5                  10                  15                  20 atg gac gat gcc ggt cgt gaa aat gaa ggt gat ctt att tgc gct gct       630
Met Asp Asp Ala Gly Arg Glu Asn Glu Gly Asp Leu Ile Cys Ala Ala
              25                  30                  35 gaa aat gtc agc act gaa caa atg gcc ttt ctt gta cgc cat tcc tca       678
Glu Asn Val Ser Thr Glu Gln Met Ala Phe Leu Val Arg His Ser Ser
          40                  45                  50 ggc tac gtc tgt gca cct atg acg aat gcc att gct gat aag ttg gac       726
Gly Tyr Val Cys Ala Pro Met Thr Asn Ala Ile Ala Asp Lys Leu Asp
      55                  60                  65 ctt cca cta ctg aga aca ggc atg aag ttt gaa tcc aat gat gac gac       774
Leu Pro Leu Leu Arg Thr Gly Met Lys Phe Glu Ser Asn Asp Asp Asp
  70                  75                  80 agg cat gga act gca tac aca ata act gta gat gta gcc caa ggc act       822
Arg His Gly Thr Ala Tyr Thr Ile Thr Val Asp Val Ala Gln Gly Thr
 85                  90                  95                 100 acc aca ggt att tct gct cac gac agg tcg atg act tgt agg gct ctt       870
Thr Thr Gly Ile Ser Ala His Asp Arg Ser Met Thr Cys Arg Ala Leu
             105                 110                 115 gca gac tct tcc tct acg cca aaa tca ttt tta aaa cca ggg cac atc       918
Ala Asp Ser Ser Ser Thr Pro Lys Ser Phe Leu Lys Pro Gly His Ile
         120                 125                 130 tgt ccc ttg aga gcc gct gat ggc ggt gtt ttg cag aga aga ggc cac       966
Cys Pro Leu Arg Ala Ala Asp Gly Gly Val Leu Gln Arg Arg Gly His
     135                 140                 145 act gag gcc ggt gtc gat ttg tgt aaa cta agt gga cta agt ccc gtc      1014
```

-continued

```
Thr Glu Ala Gly Val Asp Leu Cys Lys Leu Ser Gly Leu Ser Pro Val
    150                 155                 160
gct gtt att ggc gaa ttg gtt aac gat gac gaa caa gga act atg atg    1062
Ala Val Ile Gly Glu Leu Val Asn Asp Asp Glu Gln Gly Thr Met Met
165                 170                 175                 180 aga tta aat gac tgc caa gcg ttt ggt aag aaa cat gcc att cct ttg    1110
Arg Leu Asn Asp Cys Gln Ala Phe Gly Lys Lys His Gly Ile Pro Leu
            185                 190                 195 atc tcc atc gaa gaa ttg gcc caa tat ttg aag aaa taa tctggtgaac    1159
Ile Ser Ile Glu Glu Leu Ala Gln Tyr Leu Lys Lys
                200                 205 attttctcca ttcattctat cacaacagac tcacacatat atacatgtat atatttgtaa    1219
ctttgtatat atcttttgtt ttttgacctt tttcttcctc tatgttttc agccatacaa     1279 aaatatggga ttttagcaa gagaaaaagt acatctaaaa aaagtagtaa taggaggaag     1339
ccaagattgg ttgaaacaca gttataaact cttcaaggca attatgaaca ggattttcgg     1399
atatgggaac aaaagagcc atgatcagct cttacaagag tcgaatcagt ccatgaatca     1459
ggcccaacaa tcactatcga acagaatatc ccagttagat actcaaatcg cccagttaaa     1519
cttccagctg d                                                         1530
```

<210> SEQ ID NO 6
<211> LENGTH: 208
<212> TYPE: PRT
<213> ORGANISM: Saccharomyces cerevisiae

<400> SEQUENCE: 6

```
Met Phe Thr Pro Ile Asp Gln Ala Ile Glu His Phe Lys Gln Asn Lys
  1               5                  10                  15

Phe Val Ile Val Met Asp Asp Ala Gly Arg Glu Asn Glu Gly Asp Leu
                 20                  25                  30

Ile Cys Ala Ala Glu Asn Val Ser Thr Glu Gln Met Ala Phe Leu Val
             35                  40                  45

Arg His Ser Ser Gly Tyr Val Cys Ala Pro Met Thr Asn Ala Ile Ala
         50                  55                  60

Asp Lys Leu Asp Leu Pro Leu Leu Arg Thr Gly Met Lys Phe Glu Ser
 65                  70                  75                  80

Asn Asp Asp Asp Arg His Gly Thr Ala Tyr Thr Ile Thr Val Asp Val
                 85                  90                  95

Ala Gln Gly Thr Thr Thr Gly Ile Ser Ala His Asp Arg Ser Met Thr
            100                 105                 110

Cys Arg Ala Leu Ala Asp Ser Ser Thr Pro Lys Ser Phe Leu Lys
        115                 120                 125

Pro Gly His Ile Cys Pro Leu Arg Ala Ala Asp Gly Gly Val Leu Gln
    130                 135                 140

Arg Arg Gly His Thr Glu Ala Gly Val Asp Leu Cys Lys Leu Ser Gly
145                 150                 155                 160

Leu Ser Pro Val Ala Val Ile Gly Glu Leu Val Asn Asp Asp Glu Gln
                165                 170                 175

Gly Thr Met Met Arg Leu Asn Asp Cys Gln Ala Phe Gly Lys Lys His
            180                 185                 190

Gly Ile Pro Leu Ile Ser Ile Glu Glu Leu Ala Gln Tyr Leu Lys Lys
        195                 200                 205
```

<210> SEQ ID NO 7
<211> LENGTH: 1301

-continued

```
<212> TYPE: DNA
<213> ORGANISM: Saccharomyces cerevisiae
<220> FEATURE:
<221> NAME/KEY: 5'UTR
<222> LOCATION: (1)..(469)
<221> NAME/KEY: CDS
<222> LOCATION: (470)..(979)
<221> NAME/KEY: 3'UTR
<222> LOCATION: (980)..(1301)

<400> SEQUENCE: 7
```

| | |
|---|---:|
| aatatgaagc tggacatctt gtatgcgctt ggttagtcga aatgctggag atgagctgct | 60 |
| gaagcatctg tttgtgctgt tggtttgata tgcttctcta aaccaaaaaa tttcagccga | 120 |
| tcaggtccgg gtcacaccac taccttact agtaaacaat gatggctttc attaaggtaa | 180 |
| ctttaagtga ggtggatgga agtaggttcc acgaaacttc atcgaagagg tctgggttc | 240 |
| tatggcatat agttaaaact ctgaaaggtt ttcggaggtt cccgtagtca tttcttaagg | 300 |
| ctctatgaca tattctggga gcggagatat tttcggaggt ccccgttaat aagagaaaag | 360 |
| tagccatata aagagaaca atgaaatatt gtcccagaga gtgggttcaa agcatgaaa | 420 |
| aggaacagta taacgcagta taacgcagta taacgcagta taacgcagt atg gca gtt | 478 |
|                                                                                            Met Ala Val | |
|                                                                                             1 | |
| aaa gga tta ggc aaa cca gat caa gtt tat gac ggt tcc aaa atc agg<br>Lys Gly Leu Gly Lys Pro Asp Gln Val Tyr Asp Gly Ser Lys Ile Arg<br> 5                       10                   15 | 526 |
| gtc ggt atc att cat gcc cgt tgg aac cgt gtc att att gac gct ctt<br>Val Gly Ile Ile His Ala Arg Trp Asn Arg Val Ile Ile Asp Ala Leu<br>20                  25                  30                  35 | 574 |
| gta aaa ggt gct att gaa aga atg gtt tcc ctt ggt gtc gag gaa aag<br>Val Lys Gly Ala Ile Glu Arg Met Val Ser Leu Gly Val Glu Glu Lys<br>               40                  45                  50 | 622 |
| aac ata ata att gaa act gtt cct gga tcc tat gaa tta cct tgg ggg<br>Asn Ile Ile Ile Glu Thr Val Pro Gly Ser Tyr Glu Leu Pro Trp Gly<br>                     55                  60                  65 | 670 |
| aca aaa agg ttt gtt gac aga caa gcg aag ttg gga aag ccg cta gat<br>Thr Lys Arg Phe Val Asp Arg Gln Ala Lys Leu Gly Lys Pro Leu Asp<br> 70                   75                  80 | 718 |
| gtt gta att cct att ggt gta ctt atc aaa ggt agt aca atg cac ttt<br>Val Val Ile Pro Ile Gly Val Leu Ile Lys Gly Ser Thr Met His Phe<br>85                  90                  95 | 766 |
| gaa tac att tca gat tcc act act cac gca ttg atg aac tta caa gaa<br>Glu Tyr Ile Ser Asp Ser Thr Thr His Ala Leu Met Asn Leu Gln Glu<br>100                 105               110              115 | 814 |
| aag gtc gac atg ccc gtc att ttt ggc ctc tta act tgc atg act gaa<br>Lys Val Asp Met Pro Val Ile Phe Gly Leu Leu Thr Cys Met Thr Glu<br>                   120               125              130 | 862 |
| gaa caa gcc ctg gcc aga gct ggc atc gat gaa gcg cac tcc atg cac<br>Glu Gln Ala Leu Ala Arg Ala Gly Ile Asp Glu Ala His Ser Met His<br>              135               140               145 | 910 |
| aac cat ggt gaa gat tgg ggt gct gca gca gtg gaa atg gct gtt aag<br>Asn His Gly Glu Asp Trp Gly Ala Ala Ala Val Glu Met Ala Val Lys<br>        150               155               160 | 958 |
| ttc ggt aaa aat gct ttt tga ataagcgcag agaaatctat actatatatc<br>Phe Gly Lys Asn Ala Phe<br>165 | 1009 |
| tatatatact cactatagaa gaagcccgct ctttgattgt ttcctcttac ggtgcttcaa | 1069 |
| tgcatctttc attttgcgcc tcatatcacg ggtccaatta cctctgttag cccagaactc | 1129 |
| ctcatcccag ttcgatagca ttgtttctct tccaggagcc cttactttac tcaactgtgt | 1189 |

```
ttgtcctact aaaaatggcg attgcaaatg agggaaaaac aagaagttttt tgttatctttt     1249 atccctggat acatgtggta cgggagccgt atgcaaacct agggtgtcag ad              1301
```

<210> SEQ ID NO 8
<211> LENGTH: 169
<212> TYPE: PRT
<213> ORGANISM: Saccharomyces cerevisiae

<400> SEQUENCE: 8

```
Met Ala Val Lys Gly Leu Gly Lys Pro Asp Gln Val Tyr Asp Gly Ser
 1               5                  10                  15

Lys Ile Arg Val Gly Ile Ile His Ala Arg Trp Asn Arg Val Ile Ile
            20                  25                  30

Asp Ala Leu Val Lys Gly Ala Ile Glu Arg Met Val Ser Leu Gly Val
        35                  40                  45

Glu Glu Lys Asn Ile Ile Glu Thr Val Pro Gly Ser Tyr Glu Leu
    50                  55                  60

Pro Trp Gly Thr Lys Arg Phe Val Asp Arg Gln Ala Lys Leu Gly Lys
65                  70                  75                  80

Pro Leu Asp Val Val Ile Pro Ile Gly Val Leu Ile Lys Gly Ser Thr
                85                  90                  95

Met His Phe Glu Tyr Ile Ser Asp Ser Thr Thr His Ala Leu Met Asn
            100                 105                 110

Leu Gln Glu Lys Val Asp Met Pro Val Ile Phe Gly Leu Leu Thr Cys
        115                 120                 125

Met Thr Glu Glu Gln Ala Leu Ala Arg Ala Gly Ile Asp Glu Ala His
    130                 135                 140

Ser Met His Asn His Gly Glu Asp Trp Gly Ala Ala Val Glu Met
145                 150                 155                 160

Ala Val Lys Phe Gly Lys Asn Ala Phe
                165
```

<210> SEQ ID NO 9
<211> LENGTH: 1880
<212> TYPE: DNA
<213> ORGANISM: Saccharomyces cerevisiae
<220> FEATURE:
<221> NAME/KEY: 5'UTR
<222> LOCATION: (1)..(179)
<221> NAME/KEY: CDS
<222> LOCATION: (180)..(896)
<221> NAME/KEY: 3'UTR
<222> LOCATION: (897)..(1880)

<400> SEQUENCE: 9

```
gccgcccaag tactctccgg gtaccaattc cgtccttttc ttttttttcg gtaatttcca       60
tggaggaagg ttattgaact atctattagt catattccag atccatccaa atgatataaa     120
aagacggtac ttcctaacgt acatgtcaaa ccaattggtg agatcgtaac catagcaca     179 atg ttt act ggt att gta gaa tgc atg ggg act gtt ttg gaa aac aac       227
Met Phe Thr Gly Ile Val Glu Cys Met Gly Thr Val Leu Glu Asn Asn
 1               5                  10                  15 cca tat gat gac tct gaa agt gga ggt caa gga gtt tct att act att       275
Pro Tyr Asp Asp Ser Glu Ser Gly Gly Gln Gly Val Ser Ile Thr Ile
            20                  25                  30 ggc aat gcg ggg agt att ctc acc gat tgt cac gtt gga gat tca ata       323
Gly Asn Ala Gly Ser Ile Leu Thr Asp Cys His Val Gly Asp Ser Ile
        35                  40                  45
```

| | | |
|---|---|---|
| gcc gta aat ggg gta tgc ctt act gtg acc gag ttt aat aac gac tcc<br>Ala Val Asn Gly Val Cys Leu Thr Val Thr Glu Phe Asn Asn Asp Ser<br>50                   55                        60 | 371 |
| ttc aaa gtt ggg ata tca cca gaa act ata aaa cga gtc aat gtc gct<br>Phe Lys Val Gly Ile Ser Pro Glu Thr Ile Lys Arg Ser Asn Val Ala<br>65                   70                     75            80 | 419 |
| tcc tgg att caa ggc acc cag gtc aac ttg gag aga gcg gta tct caa<br>Ser Trp Ile Gln Gly Thr Gln Val Asn Leu Glu Arg Ala Val Ser Gln<br>                   85                     90                   95 | 467 |
| gac gtt agg ttc ggt ggt cat tat gta cag ggt cac gta gac act gtt<br>Asp Val Arg Phe Gly Gly His Tyr Val Gln Gly His Val Asp Thr Val<br>             100                    105                  110 | 515 |
| gct aat att gtc tca aga aga cct gag ggg aat tca att att ttt ggg<br>Ala Asn Ile Val Ser Arg Arg Pro Glu Gly Asn Ser Ile Ile Phe Gly<br>           115                   120                  125 | 563 |
| ttt cag tta aga gat caa gag tac ttt aaa tac ata gta gaa aag gga<br>Phe Gln Leu Arg Asp Gln Glu Tyr Phe Lys Tyr Ile Val Glu Lys Gly<br>130                   135                   140 | 611 |
| ttc att tgt ata gat gga act tcc ttg acc ata atc aag gtt gac cca<br>Phe Ile Cys Ile Asp Gly Thr Ser Leu Thr Ile Ile Lys Val Asp Pro<br>145                  150                 155              160 | 659 |
| ctt tcg caa ggt gga gcc ttc tat att agt atg ata aag cac acc caa<br>Leu Ser Gln Gly Gly Ala Phe Tyr Ile Ser Met Ile Lys His Thr Gln<br>                 165                   170                175 | 707 |
| gac aat gtt atc atg cct ttg aag aaa att ggc gac gag gtt aat att<br>Asp Asn Val Ile Met Pro Leu Lys Lys Ile Gly Asp Glu Val Asn Ile<br>                 180                  185                190 | 755 |
| gaa gta gat ttg act ggg aag att att gag aag caa att cta tta acg<br>Glu Val Asp Leu Thr Gly Lys Ile Ile Glu Lys Gln Ile Leu Leu Thr<br>           195                   200                  205 | 803 |
| ttg gaa aac caa ata tca aag aaa gat agt act ttg aat act atg atc<br>Leu Glu Asn Gln Ile Ser Lys Lys Asp Ser Thr Leu Asn Thr Met Ile<br>210                   215                   220 | 851 |
| tca aac att atc gag gag aag gtt aga aac tac cta aat aaa taa<br>Ser Asn Ile Ile Glu Glu Lys Val Arg Asn Tyr Leu Asn Lys<br>225                   230                   235 | 896 |
| ataaaaaatt cgtcataaat aggtttcata acgcatttt tgaagtgatc tctccatctg | 956 |
| ctgcaaaaat agtcttgtaa atgtgtgata atgatgagat tagaacttgg tactgtagct | 1016 |
| aaggtactta ggcaacttct cttcattatg tattaccatg ttctgttggt tcacgtgaca | 1076 |
| tgcaaggta taactttttc cgtacaaatt attctctcca ccttttttgt gttgttgtga | 1136 |
| aagaactttc caattattgc cactgtaacc aaccgtccct aaataccaac gacacaaaaa | 1196 |
| ctgctgctac tatgggtggt aacgttctcc ccattcatta tgaccccaaa actgttaaac | 1256 |
| aattaactaa agaagtatgt aaaattcaag aatatatctg gccctgtctt gttcaccca | 1316 |
| gaataaatcg ctaacacaag tctaattaac cttctttctc attcgtagat tactgttgca | 1376 |
| tcatgtatag gagctgccaa ggtgctctct tcagtcttgc ctcagcgctg ctgttgagaa | 1436 |
| gattttcatc agtatataga aatgtcagaa ctcaagtgcg tgttttttat cattgttctt | 1496 |
| ggatttcaat gggtgctgtc ttcagagctg ataagcaatt gctcaagttc cagacaaatt | 1556 |
| attatcgtga ggaacagaaa agaagagaaa agattatgga tgaagctgct gagagaggcc | 1616 |
| tttttctgga ggatgagagt ttgaactctt cccggtcaac tacatgaaag ttattttcat | 1676 |
| gtctacttat atattcatat atcagtgcag atggtttatt tctataaata catagacccg | 1736 |
| caaattacca cagcaatgcc ttaatgattt tagaactaaa aaaattgtga accgaatgct | 1796 |
| tctcaggacg cgaacaaaaa ccaaattgtc caaagaacta aaacaatgcc aaattccagc | 1856 | aaccgatata tggtttggtc atcd                                            1880

<210> SEQ ID NO 10
<211> LENGTH: 238
<212> TYPE: PRT
<213> ORGANISM: Saccharomyces cerevisiae

<400> SEQUENCE: 10

Met Phe Thr Gly Ile Val Glu Cys Met Gly Thr Val Leu Glu Asn Asn
1               5                   10                  15

Pro Tyr Asp Asp Ser Glu Ser Gly Gly Gln Gly Val Ser Ile Thr Ile
            20                  25                  30

Gly Asn Ala Gly Ser Ile Leu Thr Asp Cys His Val Gly Asp Ser Ile
        35                  40                  45

Ala Val Asn Gly Val Cys Leu Thr Val Thr Glu Phe Asn Asn Asp Ser
    50                  55                  60

Phe Lys Val Gly Ile Ser Pro Glu Thr Ile Lys Arg Ser Asn Val Ala
65                  70                  75                  80

Ser Trp Ile Gln Gly Thr Gln Val Asn Leu Glu Arg Ala Val Ser Gln
                85                  90                  95

Asp Val Arg Phe Gly Gly His Tyr Val Gln Gly His Val Asp Thr Val
            100                 105                 110

Ala Asn Ile Val Ser Arg Arg Pro Glu Gly Asn Ser Ile Ile Phe Gly
        115                 120                 125

Phe Gln Leu Arg Asp Gln Glu Tyr Phe Lys Tyr Ile Val Glu Lys Gly
    130                 135                 140

Phe Ile Cys Ile Asp Gly Thr Ser Leu Thr Ile Ile Lys Val Asp Pro
145                 150                 155                 160

Leu Ser Gln Gly Gly Ala Phe Tyr Ile Ser Met Ile Lys His Thr Gln
                165                 170                 175

Asp Asn Val Ile Met Pro Leu Lys Lys Ile Gly Asp Glu Val Asn Ile
            180                 185                 190

Glu Val Asp Leu Thr Gly Lys Ile Ile Glu Lys Gln Ile Leu Leu Thr
        195                 200                 205

Leu Glu Asn Gln Ile Ser Lys Lys Asp Ser Thr Leu Asn Thr Met Ile
    210                 215                 220

Ser Asn Ile Ile Glu Glu Lys Val Arg Asn Tyr Leu Asn Lys
225                 230                 235

<210> SEQ ID NO 11
<211> LENGTH: 2366
<212> TYPE: DNA
<213> ORGANISM: Saccharomyces cerevisiae
<220> FEATURE:
<221> NAME/KEY: 5'UTR
<222> LOCATION: (1)..(1344)
<221> NAME/KEY: CDS
<222> LOCATION: (1345)..(2079)
<221> NAME/KEY: 3'UTR
<222> LOCATION: (2080)..(2366)

<400> SEQUENCE: 11
tcctgtattt caactttcca tacatgaaag attctttggc cattttctta atccatttca     60
tattttcatc tgattttttt tctgtttttcc acttgctgct cattatttca ttttataatt    120
tttgcaaaca tgcaatattt cgccatatat tgagaaaagc aattcttcgt tgtttcccagt   180 aaagaaagaa caaatgcaga tttctaccgc caccgctaga ttaagaattt tttttggtta    240

```
ctgatttgaa tcacatacga tgagttttag acatttcaag aggagacttg acacaagctc      300
agcagatgaa agctcttcgg cggatgaaga gcatccagac caaaacgtat ctctaacaga      360
aaaatcagcc tcattaagcc atagtgattt gggcggcgaa attttaaatg gtacaggaaa      420
gaaccgcacc cccaatgatg gccaagaatc aaatgaaagt gatgggagtc ccgaaagtga      480
tgagagtccc gaaagtgaag aaagtagcga acagtgat tcgagcgata gtgacgatat       540 gagacctta ccgaggccat tatttatgaa gaaaaggcc ataatttgc agaaagctac         600 caagatagat caaccctgga atgcccaaga tgacgcacga gttctgcaaa caagaagga       660 aaatatgata aaaacatcg acaaagctaa tcaagtggca agaactacg aaacgatgaa       720 gctgagactt aacaccaatt acagcaccaa cgaagaattg atcaagcagt gcttgctctt      780
agatgataac gatgaagtcg attcagaaaa ggagagacag aaatggtttg aaaggcagaa       840
cgaacgaaag caaaagcata agaatacag acttgcgaaa caagagaat cagaagaata       900 tgaggcaaaa cgatttgaag cgatgcaaaa aggcaaagat gggaatacca aatacgacgt       960
tatcttggac aaggagaaag agaaacttga tcacaaaaaa caagatcgg ctgaaaaagt     1020 agaaaaatct cacaataaca accgttacaa gattacaaga actaaaaatg ttgaatttgg     1080
tgacctaggc aagaatagta gagattacga agaaactgaa tattcggtta tataacaccg     1140
catcacacac acaaacccac atgcctttca agttagttga tgtcgggaaa atcccgaaac     1200
agaaaaaaga ggcaaagatg aagatatcaa attttttcgc agaaccatta catctggctt     1260
tggatacgat gaaacaatct agcagaaata cagtaccaac ctattggtag cttctttgta     1320
ttactatcaa cattttaga agat atg tct ttg aca cca ctg tgt gaa gat         1371
                          Met Ser Leu Thr Pro Leu Cys Glu Asp
                           1               5 tta cca caa ttt ctg caa aac tat cta ccg aat gct ggt caa acg gaa       1419
Leu Pro Gln Phe Leu Gln Asn Tyr Leu Pro Asn Ala Gly Gln Thr Glu
 10              15                  20                  25 aat acc att gtg ccc ttt gtc aca cta act tat gct caa tcg ctc gac       1467
Asn Thr Ile Val Pro Phe Val Thr Leu Thr Tyr Ala Gln Ser Leu Asp
             30                  35                  40 gcg aga gta tct agg ggc cct gga gtg agg act aca att tca cat ccc       1515
Ala Arg Val Ser Arg Gly Pro Gly Val Arg Thr Thr Ile Ser His Pro
                 45                  50                  55 gag acc aaa aca atg acg cat tat ttg aga cat cat cac gat gga ata       1563
Glu Thr Lys Thr Met Thr His Tyr Leu Arg His His His Asp Gly Ile
         60                  65                  70 ctc gta gga agt gga aca gtg cta gct gat aat cct gga ttg aat tgt       1611
Leu Val Gly Ser Gly Thr Val Leu Ala Asp Asn Pro Gly Leu Asn Cys
 75                  80                  85 aaa tgg ggt ccc gat ccg gct gca aat tcc cca agg cca ata ata ata       1659
Lys Trp Gly Pro Asp Pro Ala Ala Asn Ser Pro Arg Pro Ile Ile Ile
 90                  95                 100                 105 gat aca aag caa aag tgg cga ttt gat ggt tca aaa atg caa gaa ctt       1707
Asp Thr Lys Gln Lys Trp Arg Phe Asp Gly Ser Lys Met Gln Glu Leu
             110                 115                 120 ttt att aaa cga cag ggt aag ccg cca atc gtt gtt gtc aca agt gag       1755
Phe Ile Lys Arg Gln Gly Lys Pro Pro Ile Val Val Val Thr Ser Glu
                 125                 130                 135 ccc att ata aaa gaa caa cat gta gac tac gca att tgt cca ata aat       1803
Pro Ile Ile Lys Glu Gln His Val Asp Tyr Ala Ile Cys Pro Ile Asn
         140                 145                 150 gat act acg aaa ttg gtc gat tgg aag aaa ttg ttt gag ata tta aaa       1851
Asp Thr Thr Lys Leu Val Asp Trp Lys Lys Leu Phe Glu Ile Leu Lys
 155                 160                 165
```

```
gaa gaa ttc aat ata agg tca gta atg gtt gaa gga ggt gcc aat gta    1899
Glu Glu Phe Asn Ile Arg Ser Val Met Val Glu Gly Gly Ala Asn Val
170                 175                 180                 185 ata aat cag ttg ttg ctg agg agc gat att gtc aac agt ctt ata ata    1947
Ile Asn Gln Leu Leu Leu Arg Ser Asp Ile Val Asn Ser Leu Ile Ile
            190                 195                 200 act att gga tca aca ttt ctg ggt agc tca ggc acc gaa gtt agc cca    1995
Thr Ile Gly Ser Thr Phe Leu Gly Ser Ser Gly Thr Glu Val Ser Pro
        205                 210                 215 ccc caa aca gta aat tta aag gat atg tca tgg tgg aag ggc att acc    2043
Pro Gln Thr Val Asn Leu Lys Asp Met Ser Trp Trp Lys Gly Ile Thr
    220                 225                 230 gat gtg gtg ctt tgt gcg aga ctg gcc gat gac taa tagtgttaga         2089
Asp Val Val Leu Cys Ala Arg Leu Ala Asp Asp
    235                 240 actccacctt ctgtgtaatt tctttctgaa attagtgaaa aaaacgcgcc tttcaaattt  2149
tcatactagt gattggttta ttgcagatta tttatttcta attgtacata ttcttgttat  2209
tttatattat atgaaagggg taaatccaaa tgccactcta catacagatt ctgtaactgg  2269
cataacgacc agaggtttca cttttcttta tgattttaac tacttcgcct cttttcaatc  2329
ccaagtataa ggctacagga tcagctcttt gaattcd                           2366
```

<210> SEQ ID NO 12
<211> LENGTH: 244
<212> TYPE: PRT
<213> ORGANISM: Saccharomyces cerevisiae

<400> SEQUENCE: 12

```
Met Ser Leu Thr Pro Leu Cys Glu Asp Leu Pro Gln Phe Leu Gln Asn
 1               5                  10                  15

Tyr Leu Pro Asn Ala Gly Gln Thr Glu Asn Thr Ile Val Pro Phe Val
            20                  25                  30

Thr Leu Thr Tyr Ala Gln Ser Leu Asp Ala Arg Val Ser Arg Gly Pro
        35                  40                  45

Gly Val Arg Thr Thr Ile Ser His Pro Glu Thr Lys Thr Met Thr His
    50                  55                  60

Tyr Leu Arg His His His Asp Gly Ile Leu Val Gly Ser Gly Thr Val
 65                  70                  75                  80

Leu Ala Asp Asn Pro Gly Leu Asn Cys Lys Trp Gly Pro Asp Pro Ala
                85                  90                  95

Ala Asn Ser Pro Arg Pro Ile Ile Ile Asp Thr Lys Gln Lys Trp Arg
            100                 105                 110

Phe Asp Gly Ser Lys Met Gln Glu Leu Phe Ile Lys Arg Gln Gly Lys
        115                 120                 125

Pro Pro Ile Val Val Thr Ser Glu Pro Ile Lys Glu Gln His
    130                 135                 140

Val Asp Tyr Ala Ile Cys Pro Ile Asn Asp Thr Thr Lys Leu Val Asp
145                 150                 155                 160

Trp Lys Lys Leu Phe Glu Ile Leu Lys Glu Glu Phe Asn Ile Arg Ser
                165                 170                 175

Val Met Val Glu Gly Gly Ala Asn Val Ile Asn Gln Leu Leu Leu Arg
            180                 185                 190

Ser Asp Ile Val Asn Ser Leu Ile Ile Thr Ile Gly Ser Thr Phe Leu
        195                 200                 205

Gly Ser Ser Gly Thr Glu Val Ser Pro Pro Gln Thr Val Asn Leu Lys
```

-continued

```
        210                 215                 220
Asp Met Ser Trp Trp Lys Gly Ile Thr Asp Val Val Leu Cys Ala Arg
225                 230                 235                 240

Leu Ala Asp Asp
```

RIBOFLAVIN SYNTHESIS IN YEAST

This application is a continuation of U.S. patent application Ser. No. 08/403,768, which is now abandoned which is a 371 of PCT/EP93/03183 filed Nov. 12, 1993.

BACKGROUND OF THE INVENTION

1. Field of the Invention

The present invention relates to the genes for riboflavin biosynthesis in yeast, the proteins encoded therewith and genetic engineering processes for the preparation of riboflavin using these genes and gene products.

2. Description of the Related Art

The preparation of riboflavin by fermentation of fungi such as *Eremothecium ashbyii* or *Ashbya gossypii* is known (The Merck Index, Windholz et al., eds. Merck & Co., 1983, page 1183).

EP 405370 describes riboflavin-overproducing bacterial strains which were obtained by transformation of riboflavin biosynthesis genes from *Bacillus subtilis*.

BRIEF SUMMARY OF THE INVENTION

Since the genetics of riboflavin biosynthesis in bacteria and eukaryotes is different, the abovementioned genes from *Bacillus subtilis* are not suitable for a recombinant preparation process for riboflavin using eukaryotic production organisms such as *Saccharomyces cerevisiae* or *Ashbya gossypii*.

The object was therefore to isolate the riboflavin biosynthesis genes from a eukaryote in order therewith to make available a recombinant preparation process for riboflavin in a eukaryotic production organism.

DETAILED DESCRIPTION OF THE INVENTION

Figure 1:
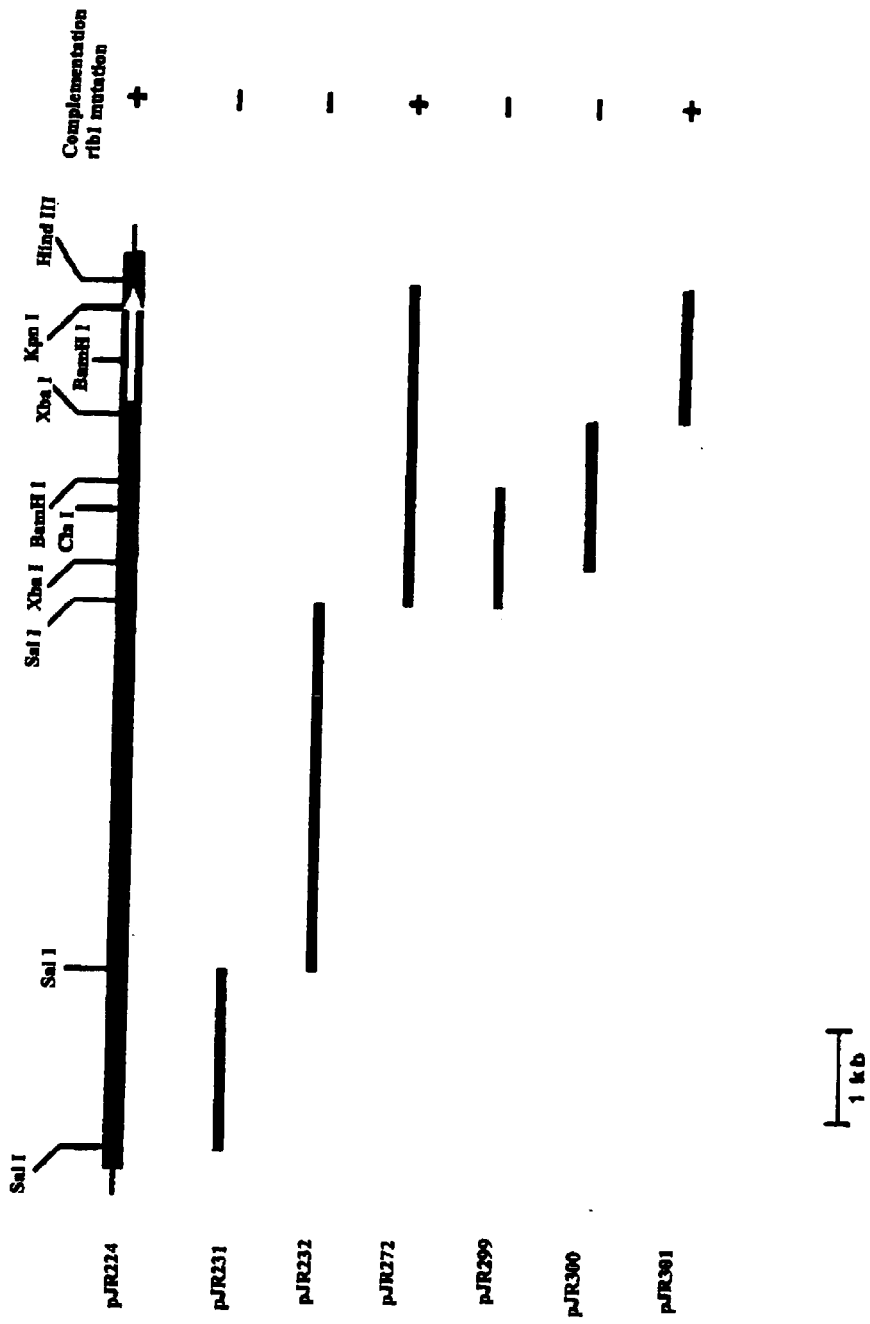
FIG. 1: shows that rib 1 gene was localized on a 1.7 kb XbaI-HindIII fragment, which was subcloned in the multicopy vector YEp352, and gave the plasmid pJR301.

Accordingly, six genes (rib genes), which encode for enzymes of riboflavin biosynthesis starting from GTP, were found in the yeast *Saccharomyces cerevisiae* and isolated.

The genes and their gene ducts (polypeptides) are shown in the sequence record by their primary structure and have the following assignment:

SEQ ID NO 1: rib 1 gene
SEQ ID NO 2: rib 1 gene product (GTP-cyclohydrolase II)
SEQ ID NO 3: rib 2 gene
SEQ ID NO 4: rib 2 gene product (DRAP (2,5-diamino-6-ribitylamino-4(3H)-pyrimidine 5' phosphate) deaminase)
SEQ ID NO 5: rib 3 gene
SEQ ID NO 6: rib 3 gene product (DBP synthase)
SEQ ID NO 12: rib 7 gene product (HTP (2,5-diamino-6-ribosylamino-4-(3H)pyrimidine 5'-phosphate) reductase)
SEQ ID NO 8: rib 4 gene product (DMRL synthase)
SEQ ID NO 9: rib 5 gene
SEQ ID NO 10: rib 5 gene product (riboflavin synthase)
SEQ ID NO 11: rib 7 gene
SEQ ID NO 12: rib 7 gene product (HTP reductase)

Guanosine triphosphate (GTP) is converted by GTP cyclohydrolase II (rib 1 gene product) to 2,5-diamino-6-ribosylamino-4-(3H)-pyrimidine-5-phosphate. This compound is then reduced by rib 7 gene product to 2,5-diamino-ribitylamino-2,4(1H, 3H)-pyrimidine-5-phosphate and then deaminated by rib 2 gene product to 5-amino-6-ribityl-amino-2,4(1H, 3H)-pyrimidinedione. The C4 compound DBP is then added in a rib 4 gene product-catalyzed reaction and 6,7-dimethyl-8-ribityllumazine (DMRL) is formed, from which riboflavin is formed in the rib 5 gene product-catalyzed reaction. The C4 compound DBP (L-3,4-dihydroxy-2-butanone-4-phosphate) is formed from D-ribulose-5-phosphate in a rib 3-gene product-catalyzed reaction.

The DNA sequences described in SEQ ID NOS 1, 3, 5, 7, 9 and 11 code for the polypeptides which are described in SEQ ID NOS 2, 4, 6, 8, 10 and 12. Apart from the abovementioned DNA sequences, also suitable are those which, as a result of the degeneration of the genetic code, have another DNA sequence, but code for the same polypeptide, The invention furthermore also relates to those DNA sequences which have a 90% homology to the abovementioned DNA sequences and code for gene products with the same biological activity. Such DNA sequences can be isolated, for example, from eukaryotes other than *Saccharomyces cerevisiae* using customary hybridization processes or the PCR technique.

The invention furthermore relates to the expression vectors which contain one or more of the DNA sequences according to the invention.

The invention likewise relates to the host organisms transformed by the DNA sequences or expression vectors according to the invention. Eukaryotic organisms, particularly preferably those of the order *Saccharomyces* or *Ashbya*, are preferably used as host organisms.

The invention furthermore includes a recombinant preparation process for riboflavin, in which the host organisms transformed according to the invention are cultured in a manner known per se by fermentation and the riboflavin formed during the fermentation is isolated from the fermentation medium and purified if desired.

The rib genes and gene products can be isolated and characterized as described in the Example and in the sequence record.

EXAMPLE

Cloning of the Riboflavin Biosynthesis Genes (Rib Genes) from Yeast

The yeast strain JC2a, which contains several suitable selection markers for transformation (Mat0, his3A1, leu2-3, 112, ura3-52) was mutagenized by treatment with EMS with the aim of introducing rib mutations. Accumulation, complementation and growth tests of riboflavin auxotrophs, which have been isolated from replica plates, confirm that the isolates with the designations AJ 126, AJ 122, JA 118, AJ21, AJ18 and AJ12 were in each case affected in one rib gene (rib 1, rib 2, rib 3, rib 4, rib 5 and rib 7).

In order to obtain the corresponding wild type copies of the six rib genes, each of the abovementioned rib mutants was transformed with 50–100 g of DNA from a genomic yeast library.

The centromere vector YCp50 was used to set up the yeast library, which can be obtained in this form from ATCC (No. 37415). The transformation was carried out by the lithium acetate method (Ito et al., J. Bacteriol. 153, 1983, 163). The transformants were selected for simultaneous uracil and riboflavin prototrophy on a synthetic complete medium without uracil and riboflavin. The frequency was $10^{-4}$ to $10^{-5}$ each according to the recipient strain. The plasmids were isolated from the positive transformants by transforming E. coli with the total yeast DNA and selecting for ampicillin resistance.

Figure 2:
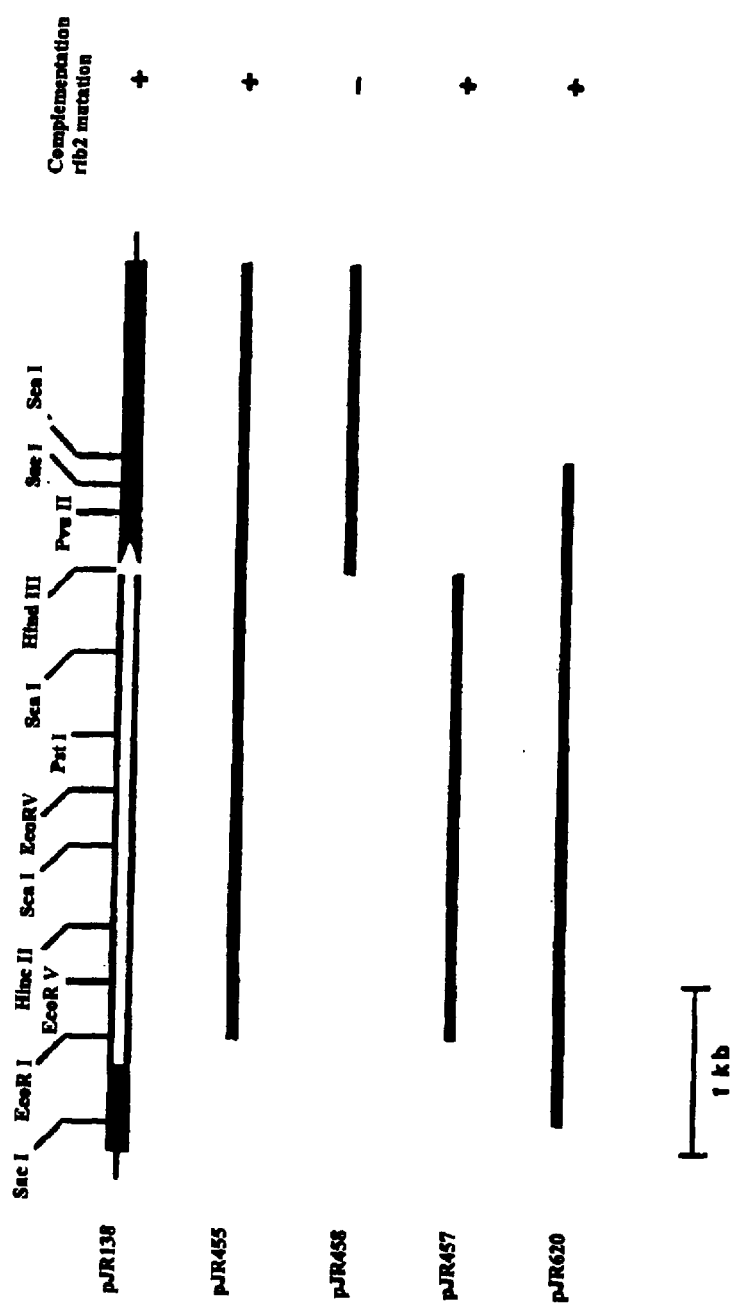
FIG. 2: shows that rib 2 gene was localized on a 2.7 kb SacI-SacI fragment, which was subcloned in pJR 620.
Figure 3:
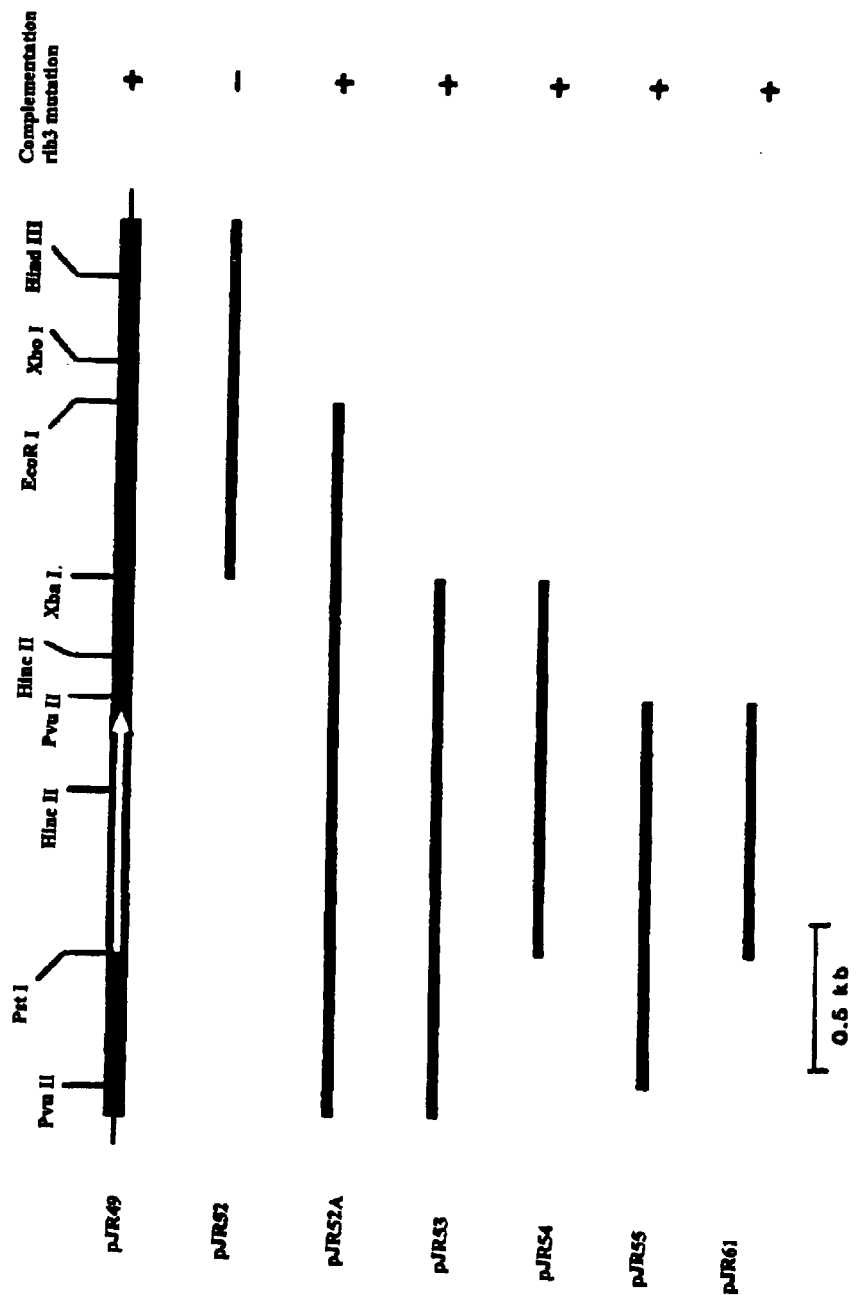
FIG. 3: shows that rib 3 gene was localized on a 1.5 kb PstI-PvuII fragment, which was subcloned in pJR61.
Figure 4:
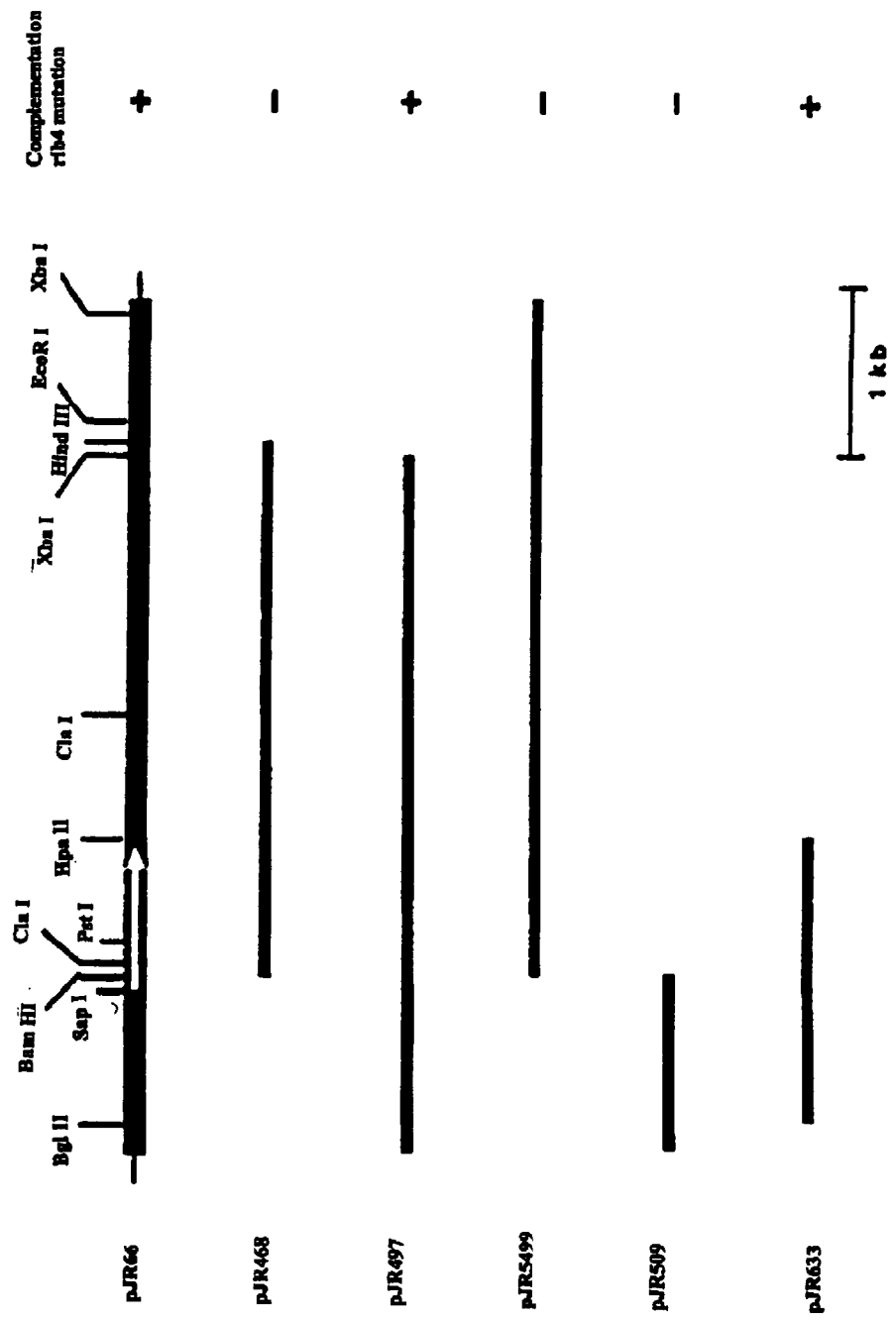
FIG. 4: shows that rib 4 gene was localized on a 1.7 kb BglI-HpaII fragment, which was subcloned in pJR633.
Figure 5:
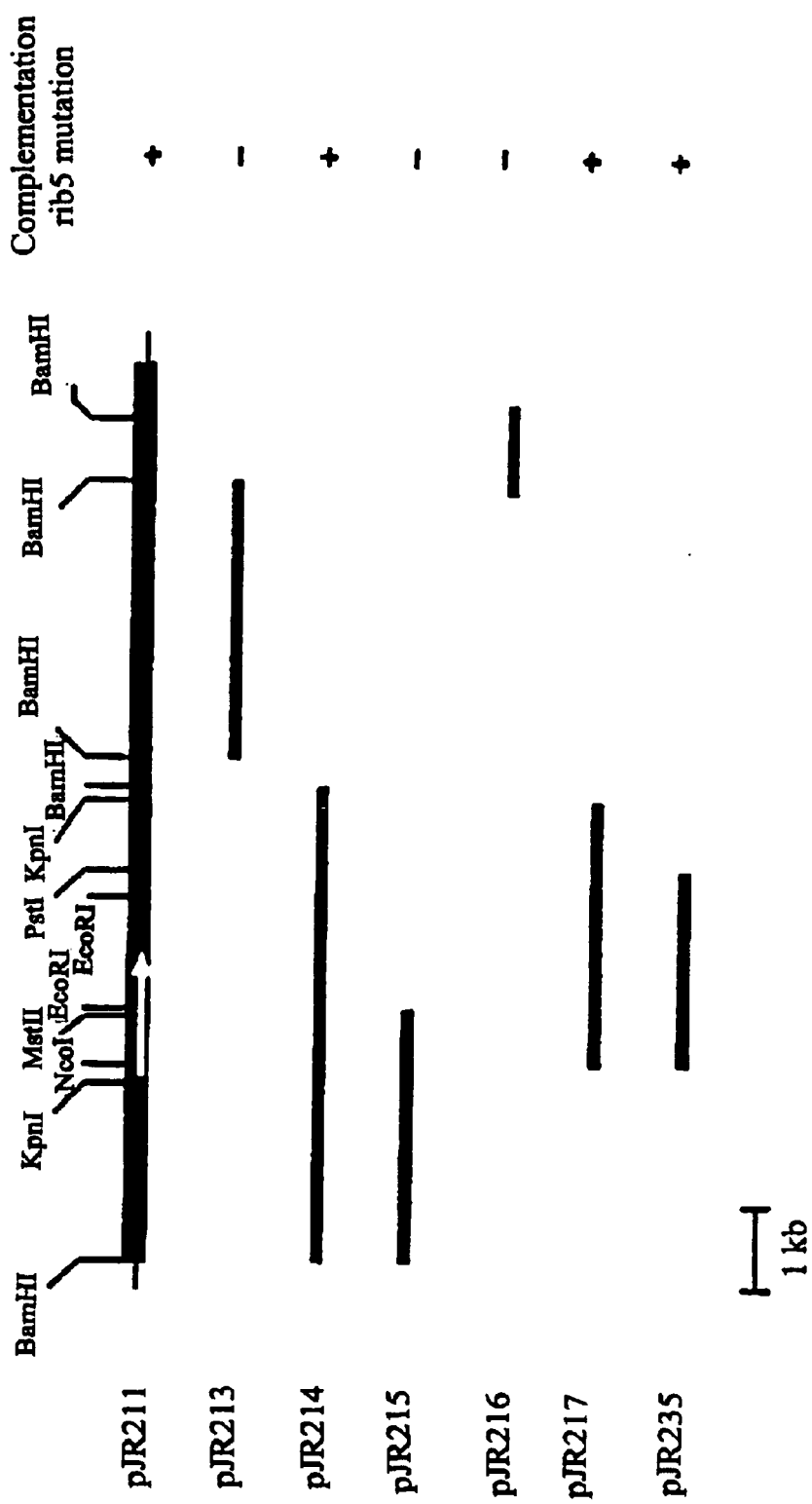
FIG. 5: shows that the rib 5 gene was localized on a 2.2 kb KpnI-PstI fragment, which was subcloned in pJR235
Figure 6:
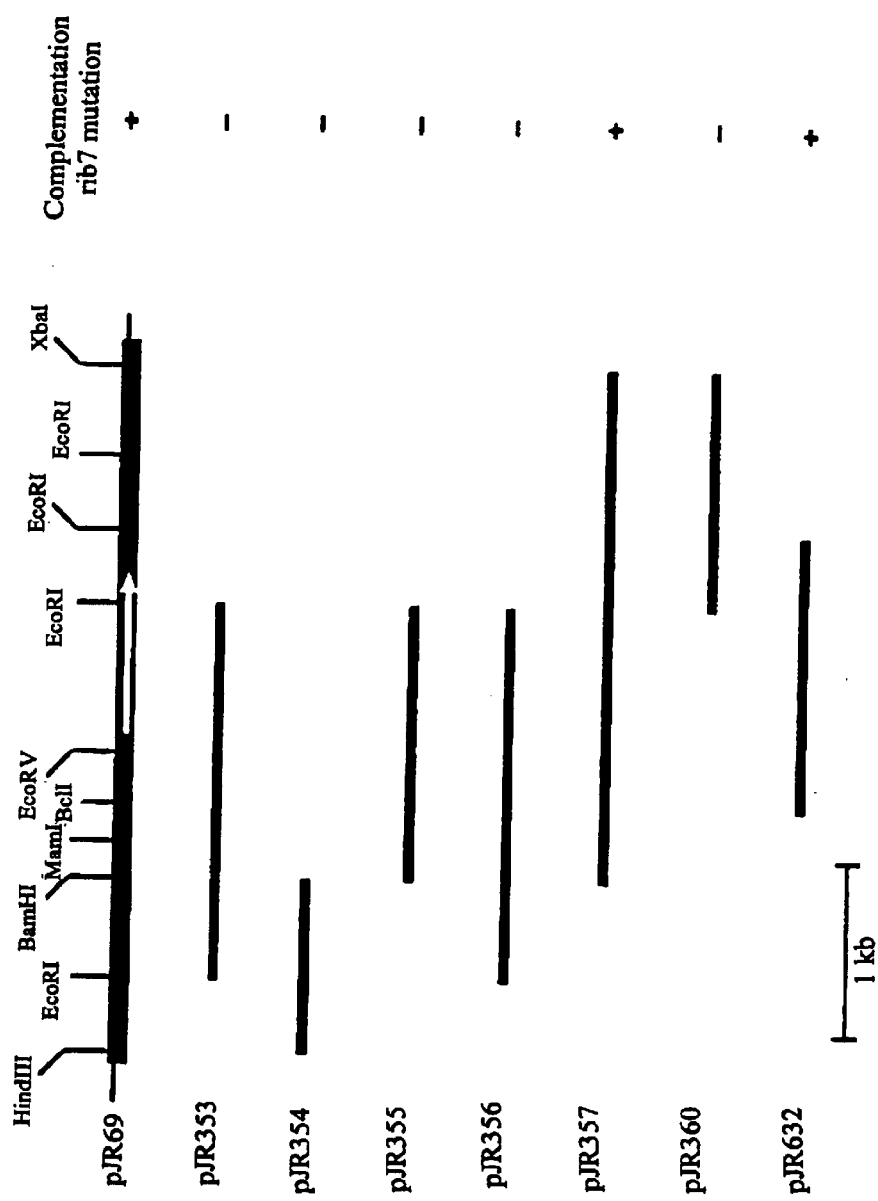
FIG. 6: shows that the rib 7 gene was localized on a 1.6 kb BclI-EcoRI fragment which was subcloned in pJR632.

The rib-complementing gene regions were localized by subcloning. As can be seen from FIG. 1, the rib 1 gene was localized on a 1.7 kb XbaI-HindIII fragment, which was subcloned in the multi-copy vector YEp352, and gave the plasmid pJR301. Correspondingly, the rib 2 gene was localized on a 2.7 kb SacI-SacI fragment (subcloned in pJR 620, FIG. 2), the rib 3 gene on a 1.5 kb PstI-PvuII fragment (subcloned in pJR61, FIG. 3), the rib 4 gene on a 1.7 kb BglI-HpaII fragment (subcloned in pJR633, FIG. 4), the rib 5 gene on a 2.2 kb KpnI-PstI fragment (subcloned in pJR235, FIG. 5) and the rib 7 gene on a 1.6 kb BclI-EcoRI fragment (subcloned in pJR632 FIG. 6).

The insertions of the corresponding pJR plasmids were sequenced in both strands with the aid of the dideoxy method of Sanger. The analysis of coding regions in all cases gave open reading frames of more than 500 bp.

| Gene  | DNA (bp)             | Polypeptide (AS)     |
|-------|----------------------|----------------------|
| rib 1 | SEQ ID NO 1 (1747)   | SEQ ID NO 2 (345)    |
| rib 2 | SEQ ID NO 3 (3086)   | SEQ ID NO 4 (591)    |
| rib 3 | SEQ ID NO 5 (1529)   | SEQ ID NO 6 (208)    |
| rib 4 | SEQ ID NO 7 (1300)   | SEQ ID NO 8 (169)    |
| rib 5 | SEQ ID NO 9 (1879)   | SEQ ID NO 10 (238)   |
| rib 7 | SEQ ID NO 11 (2365)  | SEQ ID NO 12 (244)   |

We claim:

1. A process for the recombinant preparation of riboflavin which comprises cultivating a eukaryotic organism, which has been transformed by one or more DNA sequences or an expression vector comprising one or more DNA sequences selected from the group consisting of SEQ ID NO: 2, SEQ ID NO: 4, SEQ ID NO: 8 and SEQ ID NO: 12, thereby forming a fermentation medium; and isolating the riboflavin from the fermentation medium.

* * * * *